(12) United States Patent
Illum et al.

(10) Patent No.: US 8,795,634 B2
(45) Date of Patent: Aug. 5, 2014

(54) ABSORPTION OF THERAPEUTIC AGENTS ACROSS MUCOSAL MEMBRANES OR THE SKIN

(75) Inventors: Lisbeth Illum, Nottingham (GB); Faron Michael Jordan, Coalville (GB); Andrew Lester Lewis, Nottingham (GB)

(73) Assignee: Critical Pharmaceuticals Limited, Nottingham, Nottinghamshire (GB)

( * ) Notice: Subject to any disclaimer, the term of this patent is extended or adjusted under 35 U.S.C. 154(b) by 0 days.

(21) Appl. No.: 13/063,411

(22) PCT Filed: Sep. 14, 2009

(86) PCT No.: PCT/GB2009/051188
§ 371 (c)(1),
(2), (4) Date: Mar. 10, 2011

(87) PCT Pub. No.: WO2010/029374
PCT Pub. Date: Mar. 18, 2010

(65) Prior Publication Data
US 2011/0171140 A1    Jul. 14, 2011

(30) Foreign Application Priority Data

Sep. 12, 2008 (GB) .................................. 0816642.3
Nov. 13, 2008 (GB) .................................. 0820799.5

(51) Int. Cl.
| A61K 9/12 | (2006.01) |
|---|---|
| A61K 47/14 | (2006.01) |
| A61K 31/7088 | (2006.01) |
| A61K 39/00 | (2006.01) |
| A61P 29/00 | (2006.01) |
| A61P 1/08 | (2006.01) |
| A61P 11/00 | (2006.01) |

(52) U.S. Cl.
USPC ............. 424/43; 514/785; 514/1.1; 514/44 R; 424/184.1; 977/773

(58) Field of Classification Search
None
See application file for complete search history.

(56) References Cited

U.S. PATENT DOCUMENTS

| 5,320,850 | A | 6/1994 | Gale et al. |
|---|---|---|---|
| 5,397,771 | A | 3/1995 | Bechgaard et al. |
| 6,599,528 | B1 | 7/2003 | Rosenberg et al. |
| 2001/0003589 | A1* | 6/2001 | Neuer et al. .................. 424/456 |
| 2004/0202726 | A1 | 10/2004 | DeShay |
| 2005/0058702 | A1 | 3/2005 | Ben-Sasson et al. |
| 2005/0136103 | A1 | 6/2005 | Ben-Sasson et al. |
| 2006/0067953 | A1 | 3/2006 | Mansfield et al. |
| 2006/0078616 | A1 | 4/2006 | Georgewill et al. |
| 2006/0088592 | A1 | 4/2006 | Choi et al. |
| 2007/0082016 | A1 | 4/2007 | Ottinger |
| 2007/0172517 | A1 | 7/2007 | Ben-Sasson et al. |
| 2007/0197486 | A1 | 8/2007 | Hill |
| 2007/0244085 | A1 | 10/2007 | Peracchia et al. |
| 2007/0259009 | A1 | 11/2007 | Linder |
| 2008/0194528 | A1 | 8/2008 | Barthez et al. |
| 2009/0075052 | A1 | 3/2009 | Hopf |

FOREIGN PATENT DOCUMENTS

| GB | 2221157 | A |  | 1/1990 | |
|---|---|---|---|---|---|
| IN | WO2007/077581 |  | * | 7/2007 | ............... A61K 9/26 |
| JP | 2000505090 | A |  | 4/2000 | |
| JP | 2001503406 | A |  | 3/2001 | |
| SE | WO99/32089 |  | * | 7/1999 | ............. A61K 9/107 |
| WO | 98/02187 | A2 |  | 1/1998 | |
| WO | 98/18827 | A |  | 5/1998 | |
| WO | 9932089 | A1 |  | 12/1998 | |
| WO | 99/32089 | A1 |  | 7/1999 | |
| WO | 00/00181 | A1 |  | 1/2000 | |
| WO | 01/19335 | A1 |  | 3/2001 | |
| WO | 03/070280 | A2 |  | 8/2003 | |
| WO | 03/099264 | A1 |  | 12/2003 | |
| WO | 2004/064757 | A2 |  | 8/2004 | |
| WO | 2004071498 | A1 |  | 8/2004 | |
| WO | 2005/046671 | A1 |  | 5/2005 | |
| WO | 2005058291 | A1 |  | 6/2005 | |
| WO | 2005105050 | A1 |  | 11/2005 | |
| WO | 2006024138 | A1 |  | 3/2006 | |
| WO | 2006/097793 | A2 |  | 9/2006 | |
| WO | WO2006/097793 |  | * | 9/2006 | ............. A61K 47/10 |
| WO | 2006105741 | A1 |  | 10/2006 | |
| WO | 2006108556 | A2 |  | 10/2006 | |
| WO | 2007/017331 | A2 |  | 2/2007 | |
| WO | 2007017332 | A1 |  | 2/2007 | |
| WO | 2008046905 | A1 |  | 4/2008 | |
| WO | 2008058234 | A2 |  | 5/2008 | |
| WO | 2008101344 | A1 |  | 8/2008 | |
| WO | 2009081217 | A1 |  | 7/2009 | |

OTHER PUBLICATIONS

Eskander, F.; Steckel, H; Mueller, B.W. "A Novel Formulation for cyclosporin as inhalation suspension", J. of Aerosol Medicine, Mar. 2004, v. 17(1) p. 97 abstract 18.*

Mahato, R. I. et al. "Emerging trends in Oral Delivery of Peptide and Protein Drugs", Critical Reviews in Therapeutic Drug Carrier Systems, 2003, v. 20, iss. 2&3 p. 153-214, specifically p. 159.*

(Continued)

Primary Examiner — Mina Haghighatian
Assistant Examiner — Erin Hirt
(74) Attorney, Agent, or Firm — LeClairRyan, a Professional Corporation

(57) ABSTRACT

Absorption of a therapeutic agent across a mucosal membrane or the skin can be enhanced using an absorption enhancer comprising a hydroxy fatty acid ester of polyethylene glycol.

27 Claims, 4 Drawing Sheets

(56) References Cited

OTHER PUBLICATIONS

Bosquillon, C. Pulmonary delivery of growth hormone using dry powders and visualization of its local fate in rats. Journal of Controlled Release, 2004, v. 96, pp. 233-244.*

Buggins, et al. "The Effects of Pharmaceutical Excipients on Drug Disposition," Advanced Drug Delivery Reviews 59:1482-1503 (2007).

Lindenberg, et al. "Classification of Orally Administered Drugs on the World Health Organization Model list of Essential Medicines According to the Biopharmaceutics Classification System," European Jour. of Phar. and Biophar. 58:265-278 (2004).

Wu et al. "Predicting Drug Disposition via Application of BCS: Transport/Absorption/Elimination Interplay and Development of a Biopharmaceutics Drug Disposition Classification System," Pharm. Research 22(1):11-23 (2005).

Great Britain Search Report for GB0916028.4, completed Jan. 15, 2010.

European Search Report for PCT/GB2009/051188, completed Dec. 22, 2009.

Illum, "Nasal Drug Delivery—Possibilities, Problems and Solutions," J. Control. Rel. 87:187-198 (2003).

Lloyd et al., "Azopolymers: A Means of Colon Specific Drug Delivery?" Internat. J. Pharm. 106:255-260 (1994).

Schacht et al., "Biomedical Applications of Degradable Polyphosphazenes," Biotechnol. Bioeng. 52:102-108 (1996).

Schaffazick et al., "Nanocapsules, Nanoemulsion and Nanodispersion Containing Melatonin: Preparation, Characterization and Stability Evaluation," Pharmazie 62:354-360 (2007).

Tamada et al., "The Development of Polyanhydrides for Drug Delivery Applications," J. Biomater. Sci. Polymer Edn. 4 (3):315-353 (1992).

Tracy et al., "Development and Scale-up of a Microsphere Protein Delivery System," Biotechnol. Prog. 14:108-115 (1998).

Champion et al., "Making Polymeric Micro- and Nanoparticles of Complex Shapes," Proc. Natl. Acad. Sci. U.S.A. 104:11901-11904 (2007).

Almeida et al., "Solid Lipid Nanoparticles as a Drug Delivery System for Peptides and Proteins," Adv. Drug Del. Rev. 59:478-490 (2007).

Heller, "Use of Poly(ortho esters) and Polyanhydrides in the Development of Peptide and Protein Delivery Systems," ACS Symposium Series 567:292-305 (1994).

Gonzalez et al., "Improved Oral Bioavailability of Cyclosporin A in Male Wistar Rats. Comparison of a Solutol HS 15 Containing Self-Dispersing Formulation and a Microsuspension," Internat. J. Pharm. 245:143-151 (2002).

Chattopadhyay et al., "Production of Solid Lipid Nanoparticle Suspensions Using Supercritical Fluid Extraction of Emulsions (SFEE) for Pulmonary Delivery Using the AERx System," Adv. Drug Del. Rev. 59:444-453 (2007).

Cornaire et al., "Impact of Excipients on the Absorption of P-Glycoprotein Substrates in Vitro and in Vivo," Internat. J. Pharm. 278:119-131 (2004).

Constantino et al., "Intranasal Delivery: Physicochemical and Therapeutic Aspects," Internat. J. Pharm. 337:1-24 (2007).

Debenedetti et al., "Application of Supercritical Fluids for the Production of Sustained Delivery Devices," J. Contol. Rel. 24:27-44 (1993).

Meng et al., "Fabrication and Characterization of Needle-like Nano-HA and HA/MWNT Composites," J. Mater. Sci. Mater. Med. 19:75-81 (2008).

Cleland et al., "Solvent Evaporation Processes for the Production of Controlled Release Biodegradable Microsphere Formulations for Therapeutics and Vaccines," Biotechnol. Prog. 14:102-107 (1998).

Bittner et al., "Improvement of the Bioavailability of Colchicine in Rats by Co-Administration of D-alpha-Tocopherol Polyethylene Glycol 1000 Succinate and a Polyethoxylated Derviative of 12-Hydroxy-Stearic Acid," Arzneim-Forsch Drug Res. 52:684-688 (2002).

Illum, "Nasal Drug Delivery: New Developments and Strategies," Drug Disc. Today 23(7):1184-1189 (2002).

Sharom et al., "Linear and Cyclic Peptides as Substrates and Modulators of P-Glycoprotein: Peptide Binding and Effects on Drug Transport and Accumulation," Biochem. J. 333:621-630 (1998).

Reed et al., "Loxapine P-Glycoprotein Interactions in Vitro," Drug Metab. Lett. 6:26-32 (2012) (abstract only).

Mithani et al., "Estimation of the Increase in Solubility of Drugs as a Function of Bile Salt Concentration," Pharm. Res. 13(1):163-164 (1996).

Kholodov et al., "Clinical Pharmacokinetics Reference Book," Medicine p. 96 (1985).

Schubert et al., "Structural Investigations on Lipid Nanoparticles Containing High Amounts of Lecithin," Eur. J. Pharm. Sci. 27(2-3):226-236 (2006) (abstract only).

Berko et al., "Solutol and Cremophor Products as New Additives in Suppository Formulation," Drug Dev. Ind. Pharm. 28(2):203-206 (2002) (abstract only).

Drug Formulation Technology, Ed. L.A. Ivanova, vol. 2, pp. 25-26 (1991) (English excerpt only).

Drug Formulation Technology, Ed. T.S. Kondratieva, vol. 1, pp. 111 (1991) (English excerpt only).

* cited by examiner

ABSORPTION OF THERAPEUTIC AGENTS ACROSS MUCOSAL MEMBRANES OR THE SKIN

This application is a U.S. national stage entry under 35 U.S.C. §371 of International Patent Application No. PCT/GB2009/051188, filed Sep. 14, 2009, which claims priority from Great Britain Patent Application No. 0816642.3, filed Sep. 12, 2008 and Great Britain Patent Application No. 0820799.5, filed Nov. 13, 2008.

FIELD OF THE INVENTION

This invention relates to the enhancement of absorption of therapeutic agents across mucosal membranes or the skin. In particular, the invention concerns the use of a hydroxy fatty acid ester of polyethylene glycol for enhancing transmucosal or transdermal delivery of a pharmaceutically active therapeutic agent. The invention also relates to compositions and methods for administration of a pharmaceutically active therapeutic agent to a mucosal membrane or the skin.

BACKGROUND OF THE INVENTION

Administration of therapeutic agents to the mucosa is well known in the art. Therapeutic agents can be delivered to the nasal cavity, the vaginal cavity, pulmonarily, buccally, sublingually, rectally, orally and to the eye for the local treatment of diseases or for a systemic effect.

Delivery of drugs via the absorptive mucosa, eg the buccal, nasal, ocular, oral, sublingual, rectal, and vaginal mucosae, offers distinct advantages over other routes of administration. In particular, these body cavities are easily accessible, so administration is convenient. Therapeutic agents administered via a mucosal route, except via the gastrointestinal tract, are transported directly into the systemic circulation and therefore avoid first-pass metabolism. Mucosal routes of delivery also provide the potential for a rapid pharmacological response, especially the nasal and pulmonary routes of delivery. Lipophilic drugs such as propranolol and fentanyl are readily absorbed through the nasal mucosa, resulting in a high bioavailability.

Additionally, drugs can be absorbed directly into the CNS after nasal administration by crossing the olfactory mucosa or being transported via the trigeminal nerve system in the nasal cavity.

Despite the advantages of mucosal routes of delivery, many therapeutic agents, such as peptides and proteins and hydrophilic small molecular weight drugs, are poorly absorbed across a mucosal membrane due to their physicochemical characteristics (eg large molecular weight, hydophilicity, lability), and must therefore be administered by injection or infusion. For some of these drugs, such as insulin administered to type 1 diabetics, a multiple daily dosing by injection is necessary and results in non-compliance, especially among younger patients (Drug Discovery Today, 7, 2002, 1184-1189; J Control Rel, 87, 2003, 187-198). In particular, agents of large molecular weight and/or high hydrophilicity are poorly absorbed across mucosal membranes.

The mucosal membranes provide a protective barrier against the outside environment and are lined by epithelial cells which provide a barrier to the entry of toxins, bacteria and viruses. Pathways involved with transport of therapeutic agents across mucosal membranes include transcellular and paracellular transport. In the transcellular route, therapeutic agents may be transported by a passive or carrier-mediated transport system. The passive, transcellular route involves permeation across the apical cell membrane, the intracellular space and basolateral membrane and is limited to relatively small hydrophobic compounds. Larger compounds may be absorbed by endocytosis, but this mechanism is selective, eg to particular classes of molecule and structural analogues of naturally transported analogues, and generally excludes compounds of a highly polar nature. Paracellular transport allows larger more hydrophilic therapeutic agents across mucosal membranes by passive diffusion across the intercellular junctions of the epithelium. Paracellular transport of therapeutic agents is therefore restricted by the tight epithelial junctions.

Thus, agents that are poorly absorbed across the mucosal membranes may include small molecules that are hydrophilic. Examples include morphine and other similar opioids. More commonly, they are large, high molecular weight molecules and transport is inhibited on account of their size and their hydrophilicity. This is a particular problem for biologic drugs or "biologics", such as peptides and proteins, polynucleic acids, SiRNA, RNA and antigens, since these are mostly large molecular weight molecules of a polar nature. This problem is exacerbated by the discovery of increasing numbers of biologics due to growth in biotechnology research and scientific advances.

A further problem regarding the delivery of biologics, is that biologics are prone to degradation by enzymes such as peptidases and proteases, especially when administered via the gastrointestinal tract. Delivery through a mucosal membrane such as that found lining the nasal cavity would provide an important alternative route of delivery with limited enzymatic degradation.

In order to improve the transport of these drugs across mucosal surfaces formulations that include absorption enhancers have been employed with some success, especially when delivered by nasal administration. Absorption agents used to date include surfactants, gelling microspheres and the bioadhesive polymer, chitosan. Examples of these systems have been reviewed by Illum and Fisher in "Inhalation Delivery of Therapeutic Peptides and Proteins", Adjei and Gupta (eds.) Marcel Dekker Inc, New York (1997), 135-184 and by Costantino, Illum, Brandt, Johnson and Quay, Intranasal delivery: Physicochemical and Therapeutic Aspects, Int J Pharm, 337, 2007, 1-24.

However, absorption enhancers employed previously in nasal studies, such as salicylates, bile salts and bile salt derivatives, phospholipids and lysophospholipids, sodium lauryl sulphate and cyclodextrins and chitosan derivatives, have in some cases been shown to result in irritation or damage to the mucosal membrane.

A variety of other mucosal absorption enhancer systems have been developed to deliver therapeutic agents across a mucosal membrane, but problems reported have included irritation, malabsorption and clearance of the therapeutic agent preventing successful absorption into the systemic circulation. Many excipients such as polyethylene glycol and glycofurolum (U.S. Pat. No. 5,397,771) can be highly viscous and therefore unsuitable for intranasal and mucosal delivery.

WO 03/070280 describes the use of mono- and diglycerides having the formula

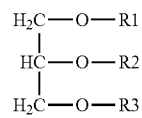

wherein R1, R2 and R3 are selected from the group consisting of from $C_6$-$C_{26}$ fatty acids, PEG polymers and hydrogen, provided that at least one of R1, R2 and R3 is a $C_6$-$C_{26}$ fatty acid residue and at least one of R1, R2 and R2 is a PEG polymer residue, for use as absorption enhancing and as mucoadhesive agents.

WO 2004/064757 describes the use of N,N-dimethylglycine, thioctic acid, sebacic acid and shikimic acid and salts thereof for enhancing the absorption of a pharmaceutically active agent through mucosal membranes.

WO 2006/097793 describes compositions for translocating therapeutically active molecules through biological membranes by including molecules in a water-soluble composition. The water-soluble composition can be immersed in a hydrophobic medium. The hydrophobic medium can consist of aliphatic, cyclic, or aromatic molecules. Examples of suitable aliphatic hydrophobic medium include mineral oil, monoglycerides, diglycerides, triglycerides, ethers and esters. Examples of suitable cyclic hydrophobic medium include terpenoids, cholesterol, cholesterol derivatives and cholesterol esters. Examples of aromatic hydrophobic medium include benzyl benzoate. The composition is further supplemented by membrane fluidizing agent which can be linear, branched, cyclical or aromatic alcohols.

WO 03/099264 describes compositions for vaginal, buccal or nasal delivery of drugs and cryoprotection of cells and embryos. The compositions consist of a non-ionizable glycol derivative in combination with a pharmaceutically active agent. The non-ionizable glycol derivative may be further combined with a mucoadhesive agent and a lipophilic or hydrophobic carrier for adhesion to, and transport through, a mucosa. A non-ionizable glycol derivative is a conjugate of aliphatic glycol or a conjugate of aliphatic glycol with aliphatic or aromatic alcohol or esters. The non-ionizable glycol derivative is selected from the group consisting of a glycol ester, glycol ether, a mixture of glycerol esters or a combination thereof.

WO2005/046671 is concerned with the formation of submicron particles of paclitaxel or its derivatives by precipitating the paclitaxel in an aqueous medium to form a pre-suspension followed by homogenisation. The particles produced generally have an average particle size of less than about 1000 nm and are not rapidly soluble. Surfactants with phospholipids conjugated with a water soluble or hydrophilic polymer are used to coat the particles. Solutol® HS15 is given as an example of a suitable surfactant, and in Example 5 it is stated that "The stabilisation that occurs as a result of homogenisation is believed to arise from rearrangement of surfactant on the surface of the particle. This rearrangement should result in a lower propensity for particle aggregation (page 31, lines 29-32)". Thus, surfactant is used to stabilise the particles and prevent agglomeration. The described particles are purported to show improved bioavailability because of increased dissolution due to their small size.

WO2006/108556 refers to the use of an admixture of surfactant and phospholipid to solubilise poorly soluble active agents, eg corticosteroids, in colloidal form. Macrogol hydroxystearate (Solutol® HS15) is one of the exemplified surfactants. The improved solubility of the active agent enables improved delivery of that agent to the intended site. For example, the formation of colloidal solutions improves delivery by nebuliser (advantages discussed on page 46 line 8-page 47, line 22).

WO99/32089 relates to a pharmaceutical composition comprising micelles in an aqueous medium, wherein the micelles comprise a lipophilic glucocortocosteriod and one and only one pharmaceutically acceptable surfactant. The surfactant is used in low concentrations of less than 5% w/w of the total composition weight (page 7, lines 1-2) in order to form micelles. A preferred surfactant is polyoxyethyleneglycol 660 12-hydroxy stearate (Solutol® HS15).

US2007/259009 refers to an aqueous pharmaceutical preparation for administration of a lightly soluble PDE4 inhibitor. Alkoxylated fats are used as cosolvent in order to obtain clear solutions having the properties necessary for parenteral preparations (paragraph [0006]). A preferred example of a suitable alkoxylated fat is Solutol® HS15 (paragraph [0016]).

WO2005/105050 and US2006/088592 describe a composition for oral delivery of a poorly absorbed drug. The composition includes the drug, an enhancer for increasing absorption of the drug through the intestinal mucosa, and a promoter, which alone does not increase the absorption of the drug, but which further increases the absorption of the drug in the presence of the enhancer. In Example 12, paclitaxel is solubilised using Solutol® or tocopheryl succinate polyethylene glycol as solubiliser. The enhancer and promoter used in Example 12 are sucrose stearate and glucosamine, respectively.

US2007/082016 relates to pharmaceutical compositions in the form of a microemulsion preconcentrate comprising a δ-amino-γ-hydroxy-ω-aryl-alkanoic acid amide renin inhibitor in an absorption enhancing carrier medium comprising (a) a lipophilic component; (b) a high HLB surfactant; and (c) a hydrophilic component. The preconcentrate provides a spontaneously dispersible water-in-oil microemulsion which upon further dilution in aqueous medium, eg gastric fluids, converts to oil-in-water microemulsion. Suitable high HLB surfactants include, but are not limited to, non-ionic efflux inhibiting and thereby absorption enhancing surfactants (paragraph [0037]). Solutol® HS15 is listed as a suitable efflux inhibitor (paragraph [0038]).

WO01/19335 is concerned with vaccine compositions in which the antigen is encapsulated in vesicles allowing delivery of the antigen through mucous membranes. The vesicles are multilamellar vesicles with an onion-like structure having an internal liquid crystal structure formed by a stack of concentric bilayers based on amphiphilic agents alternating with layers of water, an aqueous solution or a solution of a polar liquid and into which at least one antigen is incorporated. The vesicles may be formed by a wide variety of surfactants, polyethylene glycol hydroxystearate being mentioned. Preferably the compositions involve a mixture of different surfactants.

WO00/00181 relates to pulmonary drug delivery compositions useful for the inhaled delivery of corticosteroid compounds. A high HLB surfactant, preferably an ethoxylated derivative of vitamin E and/or a polyethylene glycol fatty acid ester such as Solutol® HS15 is used to solubilise the corticosteroid in order that it may be delivered by nebulisation or nasal delivery.

US2005/058702 describes an approach to facilitating the translocation across biological barriers of negatively charged molecules that are themselves unable to cross such barriers (which molecules are referred to as "effectors"). The approach involves formulating the effector with an ionic liquid forming cation. It is disclosed that the formulation may also contain a mixture of at least two substances selected from the group consisting of a non-ionic detergent, an ionic detergent, a protease inhibitor, and a reducing agent. The Examples disclosed include several such substances, including Solutol® HS15, though the concentrations of that ingredient and others are not specified. The Example formulations are said to be administered rectally or by injection into an intestinal loop.

WO 2006/024138 describes a pharmaceutical formulation having thermoreversible properties, comprising (a) an antimicrobial agent, (b) a poloxamer mixture containing at least two poloxamer polymers, and (c) a hydroxyl fatty acid ester of polyethylene glycol, wherein the formulation is solid at room temperature and is a liquid-gel at body temperature. In preferred embodiments, the hydroxy fatty acid ester of polyethylene glycol is polyethylene glycol 660 hydroxystearate. The formulation is for use in a suppository form, for administration and delivery of active pharmacological agents via the vaginal or rectal routes.

Buggins et al, "The effects of pharmaceutical excipients on drug disposition", Advanced Drug Delivery Reviews 59 (2007) 1482-1503, is a literature review describing the reported effects of commonly used co-solvents and excipients on drug pharmacokinetics and on physiological systems which are likely to influence drug disposition. The effects of Solutol® on oral absorption are discussed in part 4.3.4 on page 1497. Solutol® has been shown to increase oral absorption of the poorly soluble drug cyclosporin A. This effect was thought to be predominantly due to increased solubility of the cyclosporin in the intestinal fluid, although inhibition of CYP3A (a member of the CYP450 family of enzymes) and P-Gp may have played a part (Bravo Gonzalez et al, Improved oral bioavailability of cyclosporin A in male Wistar rats. Comparison of a Solutol® HS15 containing self-dispersing formulation and a microsuspension, Int. J. Pharm. 245 (2002) 143-151).

The paper describes how the effects of Solutol® on the oral absorption of the water-soluble drug colchicines have also been investigated. The high solubility of colchicines means that the increase in oral absorption is unlikely to be due to increased drug solubility in the intestinal fluids due to Solutol. Inhibition of P-Gp and/or CYP450 are suggested as possible mechanisms; the authors concluded that CYP450 inhibition is likely to be the major mechanism of enhanced absorption in this case, as CYP450 concentrations are high and P-Gp concentrations are low (Bittner et al, Improvement of the bioavailability of colchicine in rats by co-administration of D-alpha-tocopherol polyethylene glycol 1000 succinate and a polyethoxylated derivative of 12-hydroxy-stearic acid, Arzneim-Forsch, 52 (2002) 684-688).

It is also reported that Solutol® HS15 significantly increased digoxin transport across an everted rat gut sac in vitro, an effect attributed to the inhibition of drug efflux by P-Gp transporters (Cornaire et al, Impact of excipients on the absorption of P-glycoprotein substrates in vitro and in vivo, Int. J. Pharm. 278 (2004) 119-131).

Thus, the prior art contains numerous disclosures of the use of polyethylene glycol esters of hydroxystearic acid in pharmaceutical compositions. Such uses have, however, been restricted to the solubilisation of poorly soluble drugs and/or inhibition of P-Gp and CYP450. Indeed, Solutol® HS15 is marketed as a non-ionic solubilizer for injection solutions. The ability of such materials to enhance absorption of drugs across mucosal membranes, including hydrophilic drugs (for which solubilisation is not an issue) and/or large molecule drugs such as many biologics, has hitherto not been recognized.

There remains an urgent need for the development of efficient, non-toxic absorption enhancer systems that will enable a therapeutically relevant transport of high molecular weight and/or hydrophilic compounds across mucosal surfaces.

Transdermal drug delivery—the delivery of drugs across the skin and into systemic circulation—may also be an advantageous route of drug delivery, particularly because of the relative accessibility of the skin. However, transdermal delivery is also hampered by the problems mentioned above for drug delivery across mucosal membranes. The skin's low permeability limits the number of drugs that can be delivered in this manner, with the result that many hydrophilic compounds and/or compounds of high molecular weight are not currently deliverable by the transdermal route. Without the use of absorption enhancers, many drugs will not diffuse into the skin at a sufficient rate to obtain therapeutic concentrations. A particular concern for transdermal delivery is the possibility that a local irritation will develop at the site of application. There remains a need for the development of efficient, non-toxic absorption enhancer systems for enhancing the transport of high molecular weight and/or hydrophilic drug compounds.

We have now discovered that fatty acid esters of polyethylene glycol are able to enhance considerably the transport of a wide range of therapeutic agents across mucosal surfaces or the skin without causing irritation and without creating any damage, and thus constitute a novel group of absorption enhancers.

As noted above, hydroxy fatty acid esters of polyethylene glycol are known for their use as solubilising agents. In particular, polyethylene glycol 660 hydroxy fatty acid ester (macrogol 15 hydroxystearate) is marketed as a non-ionic solubilizer for injection solutions.

SUMMARY OF THE INVENTION

We have discovered that when a hydroxy fatty acid ester of polyethylene glycol is administered to a mucosal surface, such as the nasal cavity, in combination with a therapeutic agent, the therapeutic agent is absorbed across the mucosal surface to a much higher degree than if the hydroxy fatty acid ester of polyethylene glycol were not present in the formulation. The same absorption enhancement may be observed when a combination of a hydroxy fatty acid ester of polyethylene glycol and a therapeutic agent is administered to the skin.

Thus, according to a first aspect of the invention, there is provided the use, in a pharmaceutical composition, of an absorption enhancer comprising a hydroxy fatty acid ester of polyethylene glycol, as an agent for enhancing absorption of a therapeutic agent across a mucosal membrane or the skin.

By "enhancing absorption" across a mucosal membrane or the skin is meant an improvement in the movement or transport of the therapeutic agent across the mucosal membrane or the skin of a mammal. Generally, the increase in degree of absorption is at least 10% compared to the absorption of the composition without a hydroxy fatty acid ester of polyethylene glycol, more preferably an increase of at least 25%, or of at least 50%, and most preferably an increase of at least 100% compared to the absorption of the composition without a hydroxy fatty acid ester of polyethylene glycol.

A therapeutic agent that is absorbed across a mucosal membrane into the body may be absorbed into the local area to exhibit a local effect and/or directly into the bloodstream for systemic delivery.

The level of absorption or change in absorption may be measured or evaluated by conventional techniques, eg in terms of bioavailability, which is defined as the ratio of the concentration of therapeutic agent appearing in the blood after mucosal or transdermal administration compared to that found after intravenous administration, expressed as a percentage. Absorption may be measured or evaluated by direct or indirect means. An example of an indirect measure of absorption is the measurement of plasma glucose levels to assess the level of absorption of insulin. By definition, when a medicament is administered intravenously, its bioavailability is 100%. However, when a medicament is administered by another route (eg orally or nasally), its bioavailability normally decreases due to incomplete absorption, efflux of the absorbed drug and/or drug metabolism.

By "therapeutic agent" is meant any chemical compound or agent which is pharmacologically active and exhibits a therapeutic effect when administered to a mammal, including human subjects. It may be a synthetic or naturally-derived substance, including substances that are derived from living sources such as humans, animals or microorganisms and grown in specially engineered cells.

Therapeutic agents include but are not limited to low molecular weight drugs, nucleic acids, proteins, peptides and antigens. Nucleic acids include, but are not limited to, DNA, cDNA, RNA, siRNA, RNAi. Other large molecular weight therapeutic agents may include conjugates of such molecules, eg with polymers or cell-penetrating peptides.

In order for a drug to be absorbed into the systemic circulation it must first be in solution. Poorly soluble compounds would be expected to be poorly absorbed. When in solution, however, the compounds are available for absorption, the extent of which is dependent upon a number of other factors including:

a) The drug's hydrophobicity/hydrophilicity (partition coefficient). Hydrophobic compounds pass more readily through biological membranes, normally by the transcellular route. Hydrophilic compounds generally are less well absorbed and are transported paracellularly through the tight junctions. Proteins and peptides are generally hydrophilic and are not therefore well absorbed.

b) The size of the molecule. Smaller drug molecules pass more readily through biological membranes. Since proteins and peptides are relatively large molecules they are not well absorbed across biological membranes.

c) Active transport—influx or efflux. P-glycoprotein (P-Gp) is an ATP-dependent membrane transporter protein that actively transports xenobiotics out of cells. Immunohistochemical and functional studies have shown P-Gp to be expressed on the apical side of epithelial cells, including those found in the liver, pancreas, kidney, colon, jejunum and nasal mucosa, in mice, cows and humans. In humans, P-Gp is the product of the MDR-1 gene. By exporting absorbed drugs, P-Gp is thought to play a significant role in the disposition of its substrates, resulting in poor bioavailability and reduced activity of therapeutic compounds. Substrates of P-Gp include natural products (derived from plants, fungi, bacteria and sponges) and their minor variants, synthetic compounds and small hydrophobic peptides no longer than four amino acids long. The function of P-Gp can be studied both in vitro (in cell cultures (eg Caco-2) and ex vivo models (eg everted rat gut)) and in vivo using known substrates and inhibitors of P-Gp to probe the transporter protein's activity.

4) Drug metabolism/degradation. Enzymes present in biological cavities (such as the stomach), the liver and localised at biological membranes can degrade the drug (particularly proteins and peptides) before it enters the systemic circulation. Similarly the low pH of the stomach for example can degrade or denature drugs such as proteins and peptides, thereby preventing their absorption.

The Biopharmaceutics Classification System (BCS) is generally accepted as a guide to predict the absorption of drugs into the systemic circulation. Whilst this is generally applied to intestinal drug absorption, its principles can also be applied to other routes of drug absorption. According to the BCS System, drug substances are classified as follows:

Class I—High Permeability, High Solubility: These compounds are well absorbed and their absorption rate is usually higher than excretion.

Class II—High Permeability, Low Solubility: The bioavailability of these products is limited by their solvation rate. A correlation between the in vivo bioavailability and the in vitro solvation can be found.

Class III—Low Permeability, High Solubility: The absorption is limited by the permeation rate but the drug is solvated very fast.

Class IV—Low Permeability, Low Solubility: These compounds have a poor bioavailability. Usually they are not well absorbed over the intestinal mucosa and a high variability is expected.

The present invention is believed to be particularly suitable for enhancing the delivery of drugs that fall within Class III of the above classification, and to peptides, proteins, polynucleic acids, SiRNA, RNA and antigens that are not normally considered part of the BCS system, but which exhibit high solubility and low permeability.

According to the FDA Guidance, "Waiver of In Vivo Bioavailability and Bioequivalence Studies for Immediate-Release Solid Oral Dosage Forms Based on a Biopharmaceutics Classification System":

A drug may be considered to have "high solubility" if less than 250 ml of solvent (eg water) is required to dissolve the highest dose strength at the lowest solubility in the pH range 1-7.5. Alternatively, the threshold may be set at less than 200 ml of solvent, or less than 150 ml.

A drug substance is considered highly permeable when the extent of absorption in humans is determined to be >90% of an administered dose, based on mass-balance or in comparison to an intravenous reference dose. Alternatively, a drug may be considered to have "low permeability" if the permeation coefficient, eg measured in a Caco-2 cell monolayer, is less than $1 \times 10^{-4}$ cm/second. Alternatively, the threshold may be set at less than $1 \times 10^{-5}$ cm/second, or less than $1 \times 10^{-6}$ cm/second.

A particular advantage of the present invention is that it allows and/or improves the delivery of therapeutic agents to the respiratory tract, in particular pulmonary delivery, and to the nasal or buccal cavities. Delivery via these mucosal membranes is particularly convenient, and the therapeutic agent may be transported directly into the systemic circulation, thus avoiding degradation from stomach acid, bile, digestive enzymes and other first-pass effects. As a result, these routes of delivery provide the potential for an improved onset of action, lower dosing and more accurate dosing, and may thus enhance the efficacy and safety profile of the therapeutic agent. As an alternative to oral administration, these alternative routes would benefit patients with swallowing disorders and patients suffering from nausea.

Thus, according to a second aspect of the invention, there is provided a pharmaceutical composition comprising a therapeutic agent and an absorption enhancer comprising a hydroxy fatty acid ester of polyethylene glycol, which composition is in a form suitable for administration to the mucosal membranes of the nasal cavity, buccal cavity and/or respiratory tract.

The rapid onset of the therapeutic effect of a therapeutic agent contained in a composition according to the invention may be evaluated by determining the time after administration of the therapeutic agent when the maximum plasma concentration is reached ($T_{max}$). The $T_{max}$ when the composition is nasally administered with the absorption enhancer is relatively short, compared to the $T_{max}$ of a similar composition that does not contain the absorption enhancer. Also, experiments have shown that the nasal absorption of growth hormone and insulin may be increased by a factor of at least 2 compared with the absorption obtained after administration of a similar composition that does not contain a hydroxy fatty acid ester of polyethylene glycol.

Compositions administered to the mucosal membranes of the nasal cavity, buccal cavity and/or respiratory tract may preferably be in the form of a spray, aerosol or dry powder, including spray-dried or freeze-dried particles, microspheres or nanoparticles. Additional compositions that are preferred for buccal delivery are buccal or sublingual tablets, pastilles or lozenges, or compositions in the form of a thin film. Thin film drug delivery (also known as orally dissolving thin film) refers to a thin film strip similar in size, shape and thickness to a postage stamp, which is typically placed on or under the tongue or along the inside of the cheek and allowed to dissolve.

Despite the problems associated with delivery involving the gastrointestinal tract, oral delivery remains a popular and acceptable route for the administration of therapeutic agents. The present invention is beneficial in the oral delivery of therapeutic agents because it allows the improved transport of drugs across the gastrointestinal tract. Absorption of drugs takes place in the small intestines and the colon. Compositions for oral delivery are typically produced as tablets or capsules, or in liquid form.

Compositions in a particulate form are particularly useful for the delivery of therapeutic agents to mucosal membranes. In particular, dry powders are used for nasal delivery (nasal insufflation) and pulmonary delivery (dry powder inhalers). Solid dosage forms such as tablets, for buccal, oral and vaginal delivery, and also capsules for oral delivery, may be produced by incorporating the therapeutic agent in a particulate form.

Thus, in a particular aspect of the invention, there is provided a composition comprising a therapeutic agent and an absorption enhancer comprising a hydroxy fatty acid ester of polyethylene glycol, wherein the composition is in particulate form.

The present invention is particularly useful for the delivery of therapeutic agents that would otherwise be poorly absorbed by a mucosal membrane or the skin, and until now have preferably been administered by alternative routes such as injection or infusion. This generally applies to therapeutic agents having a large molecular weight, more specifically a molecular weight greater than 1000, and especially to large hydrophilic molecules, and also to small molecular weight molecules that are hydrophilic.

Hydrophilicity may be expressed in terms of "log P". Log P is the logarithm of the partition coefficient, P, where P is the ratio of concentrations of an un-ionized compound in the two phases of a mixture of two immiscible solvents at equilibrium, one solvent being water and the second a hydrophobic solvent, most commonly octanol. Hence log P is a measure of differential solubility of the substance between the water and the hydrophobic solvent, ie a measure of hydrophilicity or hydrophobicity. Hydrophobic compounds will have a high log P and hydrophilic compounds a low or negative log P. In general, the present invention may be useful in improving the absorption of any molecule for which log P is less than 3. Some drugs have a log P of less than 2.5, or less than 2.0, or less than 1.5, or less than 1.0, and drugs that partition preferentially in the aqueous phase will have a negative log P.

The use of a hydroxy fatty acid ester of polyethylene glycol as an agent for enhancing absorption of a hydrophilic therapeutic agent owes nothing to earlier disclosures of the use of such materials to facilitate solubilisation in aqueous media of poorly water-soluble drugs. Drugs that are hydrophilic, and hence dissolve well in aqueous media, do not require solubilisation, and hence the prior art provided no incentive to incorporate known solubilising agents in formulations of such drugs. This is also true for drugs that are not substrates for P-Gp, the absorption of which would not be expected to be influenced by inhibition of drug efflux by P-Gp transporters.

The present invention allows delivery of biologics across mucosal membranes or the skin, and this is particularly advantageous because biologic agents tend to be large molecules with molecular weights greater than 1000, which would otherwise be unsuitable for mucosal or transdermal delivery.

The present invention is believed to offer a significant advance in the delivery of therapeutic agents and hence the treatment of disease in humans and animals. In a further aspect of the invention there is provided a method of enhancing absorption of a therapeutic agent across a mucosal membrane or the skin, which method comprises (a) providing a composition comprising the therapeutic agent and an absorption enhancer comprising a hydroxy fatty acid ester of polyethylene glycol, and (b) administering the composition to said mucosal membrane or the skin.

One group of therapeutic agents that may advantageously be administered to a mammal via a mucosal route such as the nasal cavity, or via a transdermal route, in accordance with the present invention, are those intended to produce an immune response, eg antigens or vaccines. By enhancing absorption of the agent across the mucosal membrane or the skin, the resulting immune response is improved.

Nucleic acids are a further group of therapeutic agents that may advantageously be administered to a mammal via a mucosal route such as the nasal cavity, or transdermally, in accordance with the present invention. Particular examples include DNA, RNA, and SiRNA. The enhancement of absorption of the nucleic acid across the mucosal membrane or the skin results in improved expression or prevention of expression in the tissue.

DETAILED DESCRIPTION OF THE INVENTION

The compositions of the present invention comprise a hydroxy fatty acid ester of polyethylene glycol. Preferably the hydroxy fatty acid ester of polyethylene glycol is polyethylene glycol 660 hydroxy fatty acid ester (also known as macrogol 15 hydroxystearate). One source of the preferred polyethylene glycol 660 hydroxy fatty acid ester used in the experiments that are described in the Examples below is the product commercially available from BASF under the trade name Solutol® HS15. Solutol® HS15 comprises about 70% by weight of polyglycol mono- and diesters of 12-hydroxystearic acid (principally the monoester of polyethylene glycol 660 and 12-hydroxystearic acid) and about 30% by weight of free polyethylene glycol (in particular polyethylene glycol 660). Solutol® HS15 is soluble in water and ethanol. Solutol® HS15 is presently the most preferred absorption enhancer for use in the invention.

It has been found that the use of a combination of hydroxy fatty acid ester of polyethylene glycol in combination with free polyethylene glycol, as is present in Solutol® HS15, may produce superior absorption enhancement than the use of hydroxy fatty acid ester of polyethylene glycol alone. Thus, in a preferred embodiment, the absorption enhancer comprises from about 30% to about 90% by weight of hydroxy fatty acid ester of polyethylene glycol, and from about 10% to about 50% by weight of free polyethylene glycol.

In the following, the term "absorption enhancer" should be taken to mean the hydroxy fatty acid ester of polyethylene glycol or, where free polyethylene glycol is present, the combination of hydroxy fatty acid ester of polyethylene glycol and free polyethylene glycol. Where the absorption enhancer is used in the form of a commercially available product, eg Solutol® HS15, the term "absorption enhancer" may be used to denote that product, including any minor constituents present in the product. It will be appreciated that the hydroxy acid fatty acid ester may comprise more than one distinct chemical species. For instance, whilst the principal fatty acid component of the fatty acid ester of Solutol® HS15 is 12-hydroxystearic acid, other fatty acid components may also be present, eg stearic acid and palmitic acid.

The polyethylene glycol that is present in the absorption enhancer, either as a component of the of hydroxy fatty acid ester of polyethylene glycol or as free polyethylene glycol, preferably has an average molecular weight of less than 2000 Da, more preferably less than 1000 Da, and most preferably less than 800 Da. The average molecular weight of the polyethylene glycol is preferably greater than 200 Da and more preferably greater than 400 Da. The average molecular weight of the polyethylene glycol is preferably between 200 and 1000 Da, or between 400 and 800 Da. It will be appreciated that in any given grade of polyethylene glycol, there will be a distribution of molecular weights. The polyethylene glycol may also be a blend of two or more different grades, and hence the molecular weight distribution may be bi- or polymodal.

The amount of absorption enhancer present in compositions prepared in accordance with the present invention is preferably at least 0.001% by weight of the total composition, more preferably at least 0.1% by weight of the total composition, more preferably at least of 1% by weight of the total composition, more preferably at least of 2% by weight of the total composition, and most preferably at least 5% by weight of the total composition.

The amount of absorption enhancer present in compositions prepared in accordance with the present invention is preferably no more than 99% by weight of the total composition, more preferably no more than 40% by weight of the total composition, more preferably no more than 20% by weight of the total composition, more preferably no more than 15% by weight of the total composition, and most preferably no more than 10% by weight of the total composition.

The amount of absorption enhancer present in compositions prepared in accordance with the present invention is preferably 0.001% to 99% by weight of the total composition, more preferably 0.1% to 40% by weight of the total composition, more preferably 1% to 20% by weight of the total composition, more preferably 2% to 15% by weight of the total composition, and most preferably 5% to 10% by weight of the total composition. Preferably, the amount of absorption enhancer present in the composition is about 7.5%, 8%, 8.5%, 9%, 9.5% or about 10% by weight of the total composition.

The use of the absorption enhancer may be expected to enhance the absorption of any therapeutic agent across a mucosal membrane or the skin. However, the present invention is particularly useful for enhancing the absorption of therapeutic agents that would otherwise be poorly absorbed across a mucosal membrane or the skin.

The invention is useful for the delivery of small molecule therapeutic agents having a low molecular weight. By the term "low molecular weight" is meant a molecular weight of less than about 1000 Da.

The invention has particular utility for the delivery of low molecule weight therapeutic agents which are hydrophilic, eg morphine.

Low molecular weight therapeutic agents with a level of hydrophilicity that presents a problem with regard to delivery across a mucosal membrane or the skin usually have a log P value less than about 3. Examples of small drug molecules with a log P value less than 3 include morphine, alfentanyl, butorphanol and buprenorphine.

Classes of drugs for the delivery of which the invention may be of lesser value include hydrophobic drugs, one example of a class of which is corticosteroids.

The use of the absorption enhancer could improve the absorption of a therapeutic agent having log P less than 3 by at least 10%.

Examples of low molecular weight therapeutic agents for use in the present invention include, but are not limited to, acitretin, albendazole, albuterol, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetirizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Ql0, cyclobenzaprine, cyclosporine, danazol, dantrolene, dexchlorpheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, risperidone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, zolmitriptan, zolpidem, and zopiclone acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metroprolol; mezocillin sodium; mivacurium chloride; mumps viral vaccine; nedocromil sodium; neostigmine bromide; neostigmine methyl sulfate; neutontin; norfloxacin; oct-reotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR: Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine; vinorelbine; vitamin B12; warfarin sodium; yellow fever vaccine; zalcitabine; zanamavir; zolandronate; zidovudine.

As noted above, the present invention is particularly useful for the delivery of drugs that fall within Class III of the BCS. Examples of small molecule therapeutics that fall into this class are:

abacavir, acarbose, acetylcarnitine, acetyl salicylic acid, acyclovir, albuterol (salbutamol), alendronic acid, allopurinol, amiloride, amlodipine, amoxicillin, ascorbic acid, amphetamine, anastrozole, ascorbic acid, atenolol, atropine, benserazide, benznidazole, bisphosphonates, capecitabine, captopril, bidisomide, camostat, captopril, cefazolin, cefcapene pivoxil, ceflacor, cetirizine, cefmetazole, cefroxadine, chloramphenicol, choline alfoscerate, cilazapril, cimetidine, ciprofloxacin sodium, clonidine, cloxacillin, codeine, colchicine, cyclophosphamide, dicloxacillin, didanosine, diethylcarbamazine, digoxin, dolasetron, doxifluridine, enalapril, ergonovine, ergotamine tartrate, erythromycin, ethambutol, ethosuximide, famciclovir, famotidine, fexofenadine, fluconazole, fursultiamine, folinic acid, furosemide, gabapentin, ganciclovir, granisetron, hydralazine, hydrochlorothiazide, imidapril, isoniazid, lamivudine, letrozole, levitirazetam, levofloxacin, levothyroxine, lisinopril metformin, methionine, methotrexate methyldopa, s-methylmethionine, morphine, nadolol, niacin, nicorandil, nicotinamide, nifurtimox, nizatidine, olopatadine, ondansetron, oseltamivir, paracetamol, penicillamine, perindopril, phendimetrazine, phenoxymethylpenicillin, pravastatin, prednisolone, primaquine, procaterol, promethazine, propylthiouracil, pseudo-ephedrine, pyrazinamide, pyridostigmine, pyridoxine, rabeprazole, ranitidine, ribavirin, riboflavin, risedronic acid, rizatriptan, stavudine, sumatriptan, taltirelin, tamsulosin, tegafur, tenofovir, terazosin, tetracycline, thiamine, thioctic acid, topiramate, trimetazidine, trimethoprim, valacyclovir, valsartan, voglibose, zalcitabine, zidovudine, zolmitriptan.

Delivery across a mucosal membrane of therapeutic agents that are large molecules, with a high molecular weight, is often difficult. Hence, the present invention has particular utility for the delivery of large molecule therapeutic agents, in particular therapeutic agents with a molecular weight greater than about 1000, or greater than 2000, or greater than 4000.

Examples of types of large therapeutic agents suitable for use in the present invention include peptides, proteins, polynucleic acids, polysaccharides, RNA, SiRNA, antigens and antibodies that are able to complex with an appropriate complexing polymer. Specific examples of such therapeutic agents include insulin, glucagons, leuprolide, growth hormone, Parathyroid hormone, calcitonin, vascular endothelium growth factor, Erythropoietin, heparin, cyclosporine, oxytocin, tyrosine, enkephalin, tyrotropin releasing hormone, follicle stimulating hormone, leuteinising hormone, vasopressin, and vasopressin analogs, catalase, superoxide dismutase, interleukin-II, interferons, colony stimulating factor, tumour necrosis factor, melanocyte stimulating hormone, glucagon-like peptide-1 and derivatives thereof, glucagon-like peptide-2 and derivatives thereof, katacalcin, cholecystekinin-12, cholecystekinin-8, exendin, gonadoliberin-related peptide, insulin-like protein, leucine-enkephalin, methionine-enkephalin, leumorphin, neurophysin, copeptin, neuropeptide Y, neuropeptide AF, PACAP-related peptide, pancreatic hormone, peptide YY, urotensin, intestinal peptide, adrenocorticotropic peptide, epidermal growth factor, prolactin, luteinising hormone releasing hormone (LHRH), LHRH agonists, growth hormone releasing factor, somatostatin, gastrin, tetragastrin, pentagastrin, endorphins and angiotensins. Thyrotropin releasing hormone, tumour necrosis factor, granulocyte-colony stimulating factor, granulocyte-macrophage-colony stimulating factor, macrophage-colony stimulating factor, heparinase, vascular endothelial growth factor, enzymes and glycoproteins.

Since peptides and protein drugs such as insulin and human growth hormone(hGH) are hydrophilic and have a large molecular weight they are not substrates for P-Gp. Hence, the increased bioavailability that has been demonstrated using the absorption enhancer of the present invention with peptides and proteins in the nasal cavity cannot be due to inhibition of P-Gp efflux. Furthermore, since insulin and hGH are not substrates for CYP3A, the known inhibition of this drug metabolising enzyme by the absorption enhancer cannot be responsible for the increased bioavailability.

Other drugs that are not substrates for P-Gp may be identified by measuring the transport of the drug across a cell monolayer, eg of Caco-2 cells, and repeating the measurement in the presence of a known P-Gp inhibitor or under other conditions known to reduce the activity of P-Gp (eg reduced temperature). A reduction is drug transport under such conditions is indicative of the drug being a substrate for P-Gp.

Of all the specific drugs listed above, those of particular interest are those that fall into one of the categories described above as being particularly useful in the invention, eg those that are hydrophilic (eg those having a low log P value) and/or those that are not substrates for P-Gp or CYP-3A.

Compositions of the present invention comprise the absorption enhancer and a therapeutic agent, and will usually contain one or more excipients and/or a pharmaceutically acceptable carrier.

The nature of the one or more excipients will depend on various factors including the form of the composition, the nature of the therapeutic agent, the method of administration, dose and desired rate of release of the therapeutic agent etc. All excipients that are known for use in pharmaceutical compositions are contemplated for use in the present invention. Typical excipients include antiadherents, binders, bioadhesive agents, buffers, coatings, disintegrants, fillers, diluents, gelling agents, thickening agents, colours, flavourings and preservatives, sorbents, sweeteners and salts, as well as agents which are known to interact with the therapeutic agent, for example to form inclusion or salt-bridge complexes, and promote the controlled release of the therapeutic agent, such as cyclodextrins and ion exchange resins.

Pharmaceutically acceptable excipients may be used to prolong retention of the composition on the mucosa, particularly in compositions for nasal administration. Thus, compositions of the present invention may preferably comprise additional excipients such as bioadhesive agents, gelling agents or thickening agents.

Examples of suitable bioadhesive agents (substances which adhere to the mucosa) include crystalline cellulose, carbopol and hydroxypropyl cellulose. It may be desirable for compositions of the present invention to gel on contact with the mucosa, at least to some extent. Examples of suitable gelling agents include but are not limited to pectin, collagen, alginates and gelatine. Thickening agents (also referred to as viscosity enhancers) that may be included in compositions of the present invention include but are not limited to hydroxypropyl methyl cellulose (HPMC), carboxymethyl cellulose (CMC), hydroxyethyl cellulose (HEC), carbopol and methyl cellulose (MC).

In general, the absorption enhancer of the present invention may enable formulations to be developed that provide effective delivery of the therapeutic agent(s) contained in the formulations, without recourse to complex formulation types. For instance, the formulations may be free or substantially free of phospholipids or the like, and may not comprise liposomes or vesicles. Similarly, as the drugs of primary interest in relation to the invention are hydrophilic, the formulations may not be micellar solutions or microemulsions. Similarly, although additional absorption enhancers may be included, the presence of such materials may not be necessary, and the composition may be free or substantially free of additional absorption enhancers, including such materials as amino acid derivatives and aminosugars. Likewise, the composition may not contain an ionic liquid forming cation or the like.

The compositions of the present invention may be free or substantially free of poloxamers. Generally, the compositions of the present invention do not have thermoreversible properties.

By "substantially" free is meant in the context of the present application that the composition contains an amount of the ingredient in question, eg poloxamers, that is nil or is so low as to have no significant effect on the properties of the composition. The concentration of such an ingredient may therefore be less than 1% by weight of the total composition, less than 0.01% or less than 0.001% by weight of the total composition.

Compositions of the present invention may also contain one or more additional active ingredients, eg additional therapeutic agents and/or additional absorption enhancers.

Additional absorption enhancers include mucolytic agents, degradative enzyme inhibitors and compounds which modify the fluidity and permeability of mucosal cell membranes. Specific examples of additional absorption enhancers for use in the compositions of the present invention include but are not limited to cyclodextrin and cyclodextrin derivatives, bile salts, poly-L-arginine, chitosan and chitosan derivatives, phospholipids, lysophospholipids, polyacrylic acid, hyaluronic acids, sodium caprate and aminated gelatin. Additional absorption enhancers are preferably included in a total amount of up to 10% by weight of the total composition.

The present invention may be of particular utility in the delivery of therapeutic agents to the nasal cavity.

The present invention may be of particular utility in the delivery of therapeutic agents to the respiratory tract, including to the lungs.

The present invention may be of particular utility in the delivery of therapeutic agents to the buccal cavity.

The present invention may also be of utility in the delivery of therapeutic agents via the skin.

The present invention may also be of utility in the delivery of therapeutic agents by administration to the gastro-intestinal tract, eg by oral or rectal administration.

Preferred routes of delivery in which the invention may be employed are delivery to the nasal cavity, the respiratory tract and the buccal cavity.

Compositions of the present invention may be formulated and administered in any suitable form, eg a spray, aerosol, dry powder, oral tablet or capsule, buccal or sublingual tablet, pastille or lozenge, pessary, suppository, enema, drops, or a thin film.

Preferred forms of composition, useful for administration to the mucosal membranes of the nasal cavity include solutions, gels (and self-gelling compositions), powders and nasal inserts. Solutions may be administered in the form of sprays or aerosols. Powder formulations may be dry powders or pressurised aerosols.

Nasal inserts are designed to overcome the rapid mucociliary clearance of the nasal cavity, contacting the nasal mucosa and therefore delivering drug for a prolonged period of time. Suitable nasal inserts include lyophilized nasal insert formulations based on bioadhesive polymers, such as carageenan, Carbopol, chitosan, hydroxypropyl methylcellulose, sodium alginate, sodium carboxy methylcellulose, polyacrylic acid, polyvinyl pyrrolidone and xantham gum. Lyophilized inserts rehydrate on contact with the mucosal surface to form a more concentrated and viscous gel than could normally be administered easily to the nasal cavity. Other suitable forms of nasal insert include absorbent materials pre-treated with an absorption enhancer and a therapeutic agent in accordance with the present invention.

Sprays, aerosols and powders may also be suitable for administration to the respiratory tract.

Compositions suitable for delivery to the buccal cavity include solutions and gels (and self-gelling compositions), as well as buccal or sublingual tablets, pastilles or lozenges, or compositions in the form of a thin film.

For administration via the skin, preferred formulation types include creams, ointments, gels and transdermal patches.

A composition comprising a solution or dispersion in an aqueous medium can be administered as a spray or aerosol. By aerosol we refer to an airborne mist of liquid particles. The dispensing system for such a formulation may typically be a can or bottle that contains a liquid pressurised by compressed, propellant gas. Similarly, sprays of liquid particles may be produced by devices in which the liquid is pressurised by a hand-operated pump and forced through an atomizer nozzle. A typical nasal spray formulation consists of the therapeutic agent suspended or dissolved in an aqueous medium, which is filled into a bottle with a metered spray pump. Pump actuation by the patient delivers the drug in fine droplets into the nasal cavity.

Aerosol and spray devices used to administer therapeutic agents by inhalation into the lungs are commonly referred to as nebulizers. Most common are jet nebulizers which use a compressed air source to produce an aerosol. Other nebulizers that are available include electronic nebulizers, wherein the aerosol is created by the vibration of membranes or meshes. Piezoelectric and ultrasonic nebulisers may also be used.

The composition comprising a therapeutic agent in accordance with the invention may be formulated in particulate form, eg in the form of spray-dried or freeze-dried particles, microspheres or nanoparticles. The particles may be delivered as a dry powder, for example by nasal insufflation or oral inhalation, or they may be used to fill capsules, may be compressed with other excipients to form a tablet, or suspended in a pharmaceutically acceptable carrier to form a suspension or emulsion.

Powder delivery devices for nasal insufflation typically comprise a manually operated pump that produces a cloud of particles when compressed. Inhalers may be used to deliver particulate therapeutic agents to the lungs to treat respiratory diseases, eg asthma. Dry powder inhalers and metered dose inhalers (or aerosol inhalers) are common types of inhaler device. Dry powder inhalers present a measured dose of the therapeutic agent in dry powder form, usually in combination with an inert carrier such as lactose. The user inhales air through the device to entrain and disaggregate the powder to form aerosol particles that are small enough to reach the lungs. Metered dose inhalers contain a pressurized propellant gas with particles suspended in it. Actuation of the device releases a single metered dose of liquid propellant that contains the particles. The volatile propellant breaks into droplets which are rapidly evaporated, resulting in an aerosol of fine particles that is inhaled by the user.

Compositions according to the present invention may be manufactured in the form in which they are intended to be delivered, or may be supplied as separate components to be combined prior to administration. For example, it is envisaged that a particulate form of the composition comprising a therapeutic agent could be suspended or dissolved in a suitable vehicle prior to administration.

The nanoparticles herein can be produced by a range of methods as described in the literature, for instance Champion et al, Proc Natl Acad Sci USA, 104, 2007, 11901-4; Chattopadhyay et al, Adv Drug Deliv Rev, 59, 2007, 444-53; Chou et al, J Mater Sci Mater Med, 2007 Jun. 19; [Epub ahead of print]; Schaffazick et al, Pharmazie, 62, 2007, 354-60; Almeida et al, Adv Drug Deliv Rev, 59, 2007, 478-90; Muller, Colloid Carriers for Controlled Drug Delivery and Targeting, CRC Press, 1991; and Jorg Kreuter (ed), Colloidal Drug Delivery Systems, Marcel Dekker, 1994. Examples include nanoprecipitation, phase separation, emulsification, self-assembly, high pressure homogenization, complexation and ionic gelation.

The microsphere formulations herein can be produced by a range of methods as described in the literature, for instance Cleland, Solvent Evaporation Processes for the Production of Controlled Release Biodegradable Microsphere Formulations for Therapeutics and Vaccines, Biotechnol Prog, 14(1), 102-107, 1998; Tracy, Development and Scale-up of a Microsphere Protein Delivery System Biotechnol Prog, 14(1), 108-115, 1998; Debenedetti et al, Application of Supercritical Fluids for the Production of Sustained Delivery Devices, Journal of Controlled Release, 24, 1993, 27-44. The microspheres may be modified to exhibit controlled release characteristics, eg by controlling the degree of crosslinking or by the incorporation of excipients that alter the diffusional properties of the therapeutic agent.

The absorption enhancer may be incorporated in the matrix of the particles or may be adhered to the surface. The drug may be incorporated in the matrix of the particles or may be adhered to the surface of the particle.

Polymers used for production of the nanoparticles and microspheres include:

(a) synthetic biodegradable polymers such as polyesters including poly(lactic acid), poly(glycolic acid), copolymers of lactic and glycolic acid, copolymers of lactic and glycolic acid with poly(ethyleneglycol), poly(e-caprolactone), poly (3-hydroxybutyrate), poly(p-dioxanone), poly(propylene fumarate); modified polyesters such as poly(ether ester) multiblock copolymers such as those based on poly(ethylene glycol) and poly(butylenes terephthalate); poly(ortho esters) including polyol/diketene acetals addition polymers as described by Heller in ACS Symposium Series 567, 292-305, 1994; polyanhydrides including poly(sebacic anhydride) (PSA), poly(carboxybiscarboxy phenoxyphenoxyhexane) (PCPP), poly[bis(p-carboxyphenoxy)methane] (PCPM), copolymers of SA, CPP and CPM, as described by Tamada and Langer in Journal of Biomaterials Science—Polymer Edition, 3, 315-353, 1992 and by Domb in Chapter 8 of the Handbook of Biodegradable Polymers, Domb and Wiseman (ed), Harwood Academic Publishers; poly(amino acids); poly (pseudo amino acids) including those described by James and Kohn in pages 389-403 of Controlled Drug Delivery Challenges and Strategies, American Chemical Society, Washington D.C.; Polyphosphazenes including derivatives of poly [(dichloro)phosphazene], poly[(organo)phosphazenes], polymers described by Schacht in Biotechnology and Bioengineering, 52, 102-108, 1996; and azo polymers including those described by Lloyd in International Journal of Pharmaceutics, 106, 255-260, 1994;

(b) synthetic non-biodegradable polymers such as vinyl polymers including polyethylene, poly(ethylene-co-vinyl acetate), polypropylene, poly(vinyl chloride), poly(vinyl acetate), poly(vinyl alcohol) and copolymers of vinyl alcohol and vinyl acetate, poly(acrylic acid) poly(methacrylic acid), polyacrylamides, polymethacrylamides, polyacrylates, poly(ethylene glycol), poly(dimethyl siloxane), polyurethanes, polycarbonates, polystyrene and derivatives; and (c) natural polymers such as carbohydrates, polypeptides and proteins including starch, cellulose and derivatives including ethylcellulose, methylcellulose, ethylhydroxy-ethylcellulose, sodium carboxymethylcellulose; collagen; gelatin; dextran and derivatives; alginates; chitin; and chitosan.

Preferred polymers include non-biodegradable polymers such ester urethanes or epoxy, bis-maleimides, methacrylates such as methyl or glycidyl methacrylate, tri-methylene carbonate, di-methylene tri-methylene carbonate; biodegradable synthetic polymers such as glycolic acid, glycolide, lactic acid, lactide, p-dioxanone, dioxepanone, alkylene oxalates, modified polyesters such as poly(ether ester) multiblock copolymers such as those based on poly(ethylene glycol) and poly(butylenes terephthalate); and caprolactones such as gamma-caprolactone.

Typically, a polymer or combination of polymers which is inert to the therapeutic agent will be used.

Suspension formulations may be prepared by a range of methods as described in the literature, for instance in Lieberman H A, Rieger M M and Banker G S, Pharmaceutical Dosage Forms: Disperse Systems $2^{nd}$ Ed, Marcel Dekker Ltd press, 1996, which includes examples of emulsions and colloidal suspensions.

The absorption enhancing effect according to this invention can be monitored with methods known in the art and these include HPLC, LC-MS, LC-MS-MS, GC-MS, spectroscopy and ELISA assays. The enhanced absorption of the therapeutic agent can be a result of a direct effect of the absorption enhancer on the mucosal membrane or the skin.

The invention will now be illustrated by the following non-limiting examples.

EXAMPLE 1

Insulin (available from Sigma-Aldrich) was dissolved in varying concentrations of Solutol® HS15 solutions ranging from 1 to 40% w/v in 0.063M phosphate buffered saline (PBS). The formulations were then administered intranasally to Sprague Dawley rats at 4 IU/kg and blood samples taken at frequent intervals up to 2 hours after administration. Blood glucose was measured using a standard glucose meter and insulin determined in the plasma by an enzyme linked immunosorbant assay (ELISA).

A group of rats was also administered with insulin dissolved in PBS via subcutaneous injection as comparison to the intranasal doses.

Figure 1:
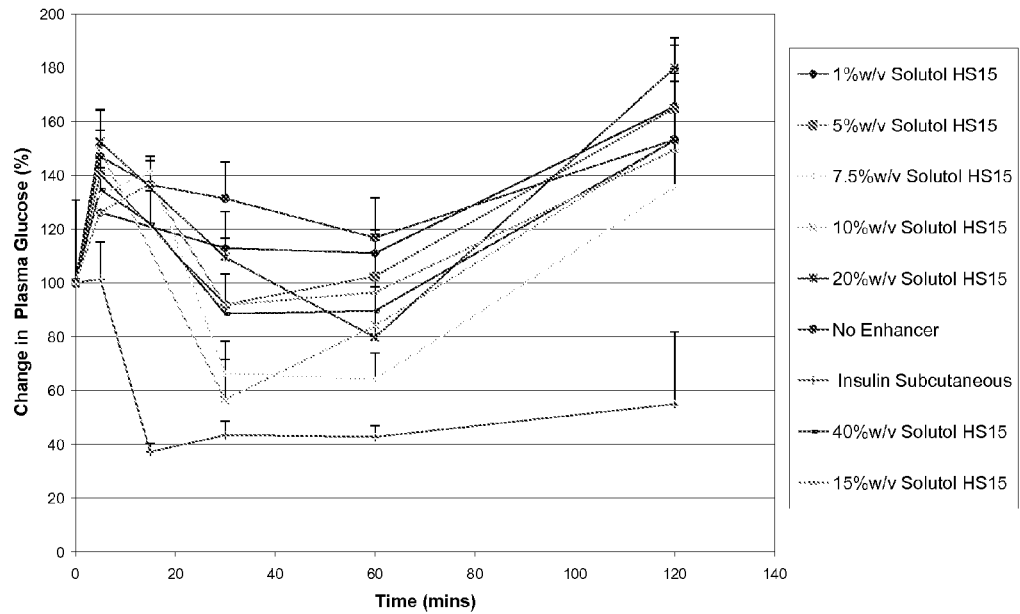
FIG. 1 shows the percentage change in blood glucose in Sprague Dawley rats following a single intranasal administration of insulin dissolved in varying concentrations of Solutol® HS15, compared to the percentage change in blood glucose following a single subcutaneous injection of soluble insulin.

The results are shown in FIG. 1.

Solutol® HS15 formulations at 7.5% and 10% w/v in PBS were most effective at promoting the transport of insulin across the nasal mucosa showing a decrease in plasma glucose levels of 70%, as compared to control insulin solutions which showed a decrease of 15%.

EXAMPLE 2

Human growth hormone (hGH) (obtained from Bioker (Sardinia)) was dissolved in a 5% w/v Solutol® HS15 solution in PBS. The solution was then administered to Sprague Dawley rats intranasally at a dose rate of 5 mg/kg and compared to a subcutaneous administration of 5 mg/kg hGH. hGH levels in the serum were determined by enzyme linked immunosorbant assay (ELISA) up to 24 hours after administration.

Figure 2:
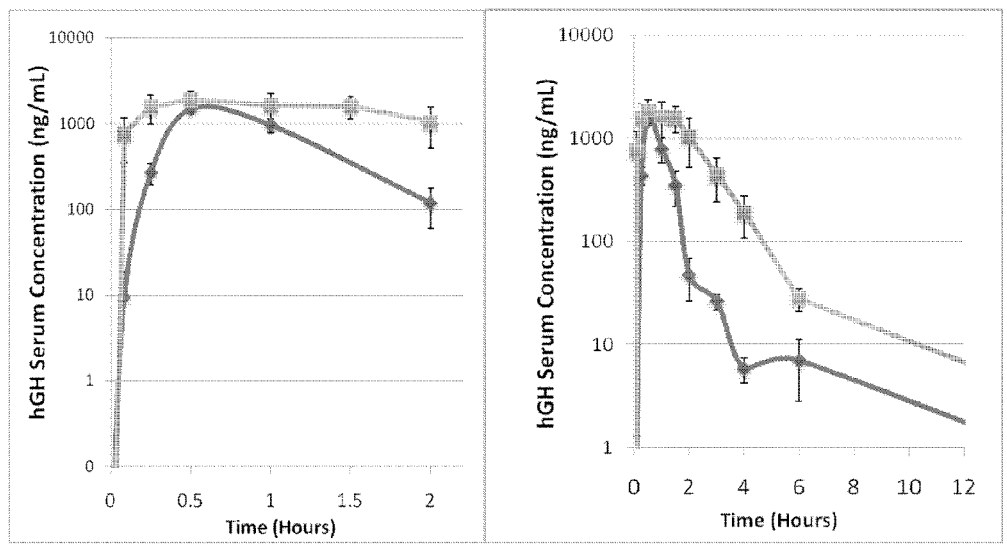
FIG. 2 shows the serum levels of human growth hormone (hGH) following a single intranasal administration of hGH in 5% w/v Solutol® HS15 and a subcutaneous injection of soluble hGH.

The results are shown in FIG. 2.

The 5% w/v Solutol® HS15 formulation was effective at enhancing the transport of hGH across the nasal mucosa with a bioavailability of 17% compared to subcutaneous administration. The bioavailability of hGH administered nasally without an absorption enhancer is less than 1%.

EXAMPLE 3

To prepare hGH loaded microparticles, micronised hGH, PLGA, PLA and Solutol® HS15 was added to a pressure vessel. The vessel was sealed and $CO_2$ was introduced. The temperature was raised to above 32° C., and the pressure increased above 76 bar. Under these conditions $CO_2$ becomes supercritical and dissolves into the polymer, which becomes liquefied. The liquefied polymer, hGH and Solutol® HS15 were then mixed and microparticles of a suitable size for injection were formed by solidification after the drug/polymer mixture was atomized and depressurised. hGH loaded microparticle formulations containing PLGA, PLA and PEG 600 were also prepared using the same method. The microparticles were administered to Sprague Dawley rats intranasally at a dose rate of 5 mg/kg hGH and compared to a subcutaneous administration of hGH. Blood samples were taken up to 24 hours after administration and hGH levels in the serum were determined by enzyme linked immunosorbant assay (ELISA).

Figure 3:
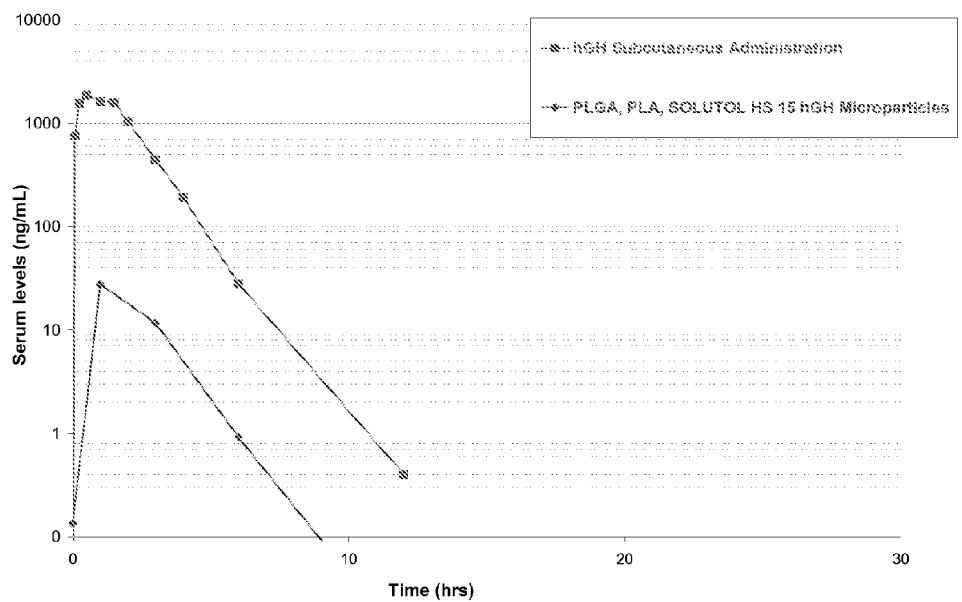
FIG. 3 shows the serum levels of hGH following a single intranasal administration of hGH microparticles prepared in supercritical carbon dioxide ($CO_2$) with poly(lactic-co-glycolide) (PLGA), polylactide (PLA) and Solutol® HS15.

The results are shown in FIG. 3.

hGH was detected in the serum after intranasal administration of the PLGA/PLA/Solutol® HS15 microparticles with a peak serum concentration of 27.6 ng/ml one hour after administration. No hGH was detected in the serum after intranasal administration of microparticles containing PLGA/PLA/Solutol® HS15.

EXAMPLE 4

This study compared the performance of the absorption enhancer of the invention with known absorption enhancers polyethylene glycol-20 stearate and chitosan chloride, for enhancing the nasal absorption of insulin in rats. The absorption enhancer of the invention that was used was the commercial product Solutol® HS15 produced by BASF, the polyethylene glycol-20 stearate was Lipopeg® 10-S, available from Lipo Chemicals Inc, and the chitosan product was Protasan® UP CL213, available from Novamatrix®. Protasan® UP CL213 is based on a chitosan in which 75-90% of the acetyl groups are deacetylated.

Insulin was dissolved in a 5% and 10% w/v solution of LipoPeg® 10-S in PBS or a 0.5% w/v solution of Protasan® UP CL213 in distilled water at pH 5.0. The formulations were compared to insulin dissolved in Solutol® HS15 at 5%, 7.5% and 10% w/v in PBS. The formulations were then administered intranasally to Sprague Dawley rats at 4 IU/kg and blood samples were taken at frequent intervals up to 2 hours after administration. Blood glucose was measured using a standard glucose meter and insulin concentrations determined in the plasma by ELISA.

Figure 4:
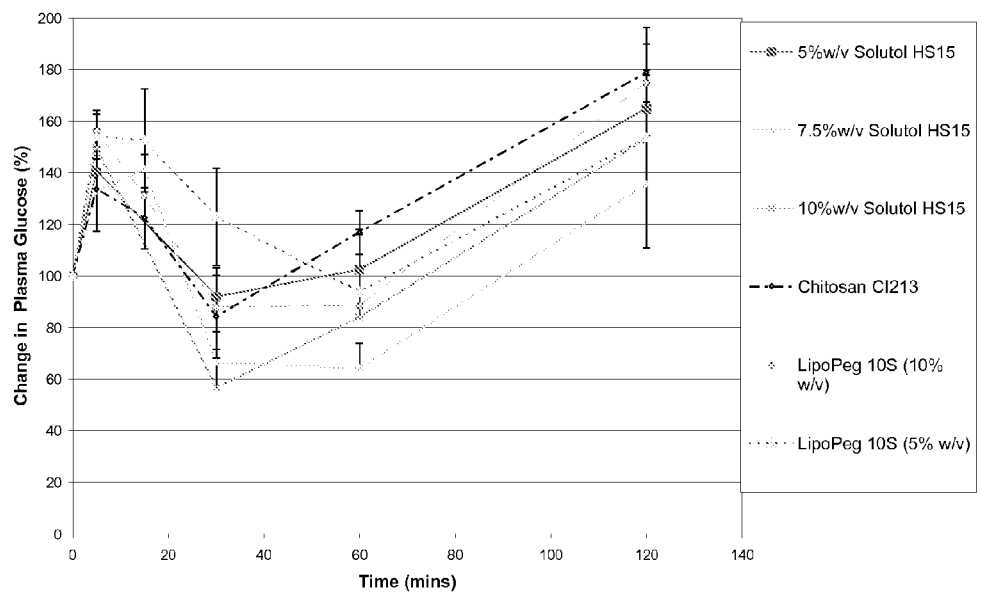
FIG. 4 shows shows the percentage change in blood glucose in Sprague Dawley rats following a single intransasal administration of insulin dissolved in Solutol® HS15, Lipopeg® 10-S and Protasan® UP CL213.

The results are shown in FIG. 4.

Solutol® HS15 at 7.5% and 10% w/v in PBS was more effective then Protasan® UP CL213 and LipoPeg® 10-S in promoting the absorption of glucose across the nasal mucosa. Insulin dissolved in Solutol® HS15 at 5% w/v in PBS gave a similar reduction in glucose compared to the Protasan® UP CL213 and the Lipopeg® 10-S concentrations tested.

EXAMPLE 5

Preparation of a Solution for Intranasal Administration Containing 7.5% w/v Solutol® HS15 and human Growth Hormone (hGH)

Ingredients
100 ml 0.063M phosphate buffered saline (PBS)
7.5 g Solutol® HS15
10 mg hGH
Method
To 100 ml of PBS was added 7.5 g of Solutol® HS15. The solution was gently heated to 40° C. whilst stirring until a clear solution was produced and all the Solutol® HS15 had dissolved. The solution was then stored at 2-8° C. prior to use. 1 ml of the 7.5% w/v Solutol® HS15 solution was then added to 10 mg of hGH. The solution was ready for intranasal dosing once all the hGH had dissolved.

EXAMPLE 6

Preparation of a Suspension of hGH Loaded Microparticles for Intranasal Administration Ingredients
0.5 g carboxy methyl cellulose
5 g mannitol
0.1 ml Tween 80
100 ml distilled water
250 mg hGH loaded PLGA/PLA/Solutol® HS15 microparticles Method
hGH loaded microparticles manufactured with PLGA, PLA and Solutol® HS15 were prepared using supercritical $CO_2$ with a particle size below 100 µm. An aqueous injection vehicle consisting of 0.5% w/v carboxy methyl cellulose, 5.0% w/v mannitol and 0.1% v/v Tween 80 was prepared. 250 mg of microparticles were suspended in 1 ml of injection vehicle and administered intranasally by pipette at the required dose rate.

EXAMPLE 7

Preparation of a Solution for Intranasal Administration Containing 40% w/v Solutol® HS15 and Risperidone Ingredients
213 mg risperidone
4 g Solutol® HS15
10 ml distilled water
Method
The risperidone and Solutol® HS15 were mixed and the mixture heated to 60° C. The water was also heated to 60° C. and stirred thoroughly into the mixture. The formulation was then ready for intranasal delivery.

EXAMPLE 8

Comparison of the Effect of a Hydroxy Fatty Acid Ester of Polyethylene Glycol, Free Polyethylene Glycol and a Combination of Two Such Substances The following materials were investigated:
Polyethylene glycol 600 (PEG600)
Polyethylene glycol-12-Hydroxystearic acid (PEG-HSA)
Polyethylene glycol-12-Hydroxystearic acid-Polyethylene glycol (HSA-PEG-HSA)
12-Hydroxystearic acid (HSA)
Solutol® HS15

The PEG-HSA and HSA-PEG-HSA were prepared by refluxing polyethylene glycol 600 (PEG 600) and 12-Hydroxystearic acid (HSA) under argon at 120° C. using methane sulfonic acid. All chemicals were purchased from Sigma Aldrich.

Four components were tested in vivo. The following components were dissolved into 0.063M phosphate buffer at the concentrations below:
PEG 600—10% w/v solution
PEG-HSA—10% w/v Solution
HSA—0.37% solution
HSA-PEG-HSA—2% solution
The lower concentrations of HSA and HSA-PEG-HSA were used due to restricted solubility of these materials.

The components dissolved in phosphate buffer were then used to prepare 1 mg/mL insulin solutions and administered intranasally to male Sprague Dawley rats at a rate of 4 IU/kg. All formulations were administered with a Gilson pipette and the tip was inserted approximately 5 mm into the nostril. The animals were housed in limited access rooms where the temperature and humidity were maintained at 21° C.±2° C. and 55%±15% relative respectively; the rooms were lit with artificial light for 12 hours each day. Blood samples were collected from the tail vein of the rats at 0 min (Pre-dose) and 5, 15, 30, 60 and 120 minutes after administration into heparinized tubes, centrifuged and the plasma collected. Blood glucose was measured immediately at each sampling point using a one touch Ultra 2 glucose meter (LifeScan, UK).

Figure 5:
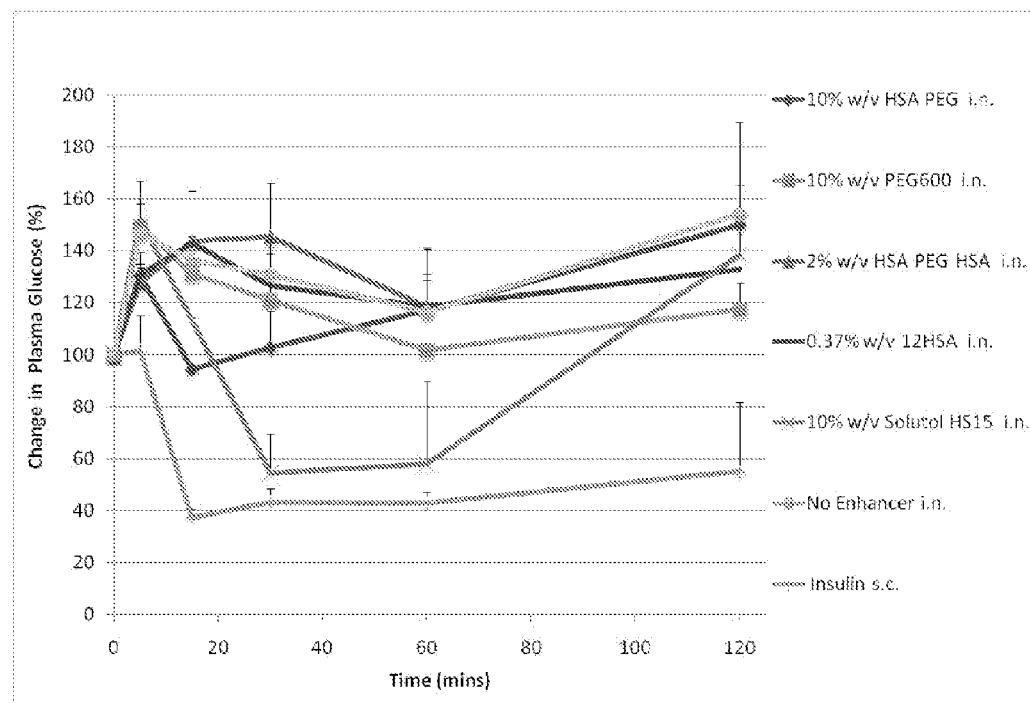
FIG. 5 shows the percentage change in blood glucose after intranasal administration of insulin with Solutol® HS15, individual components of Solutol® HS15, and a subcutaneous injection of insulin.

The blood glucose levels in FIG. 5 show that, in these experiments, the Solutol® HS15 produced a substantial drop in blood glucose levels, whereas the individual materials (PEG, PEG-HSA, HSA, HSA-PEG-HSA), at the concentrations used in these experiments and with the particular therapeutic agent studied, did not. Hence, it can be concluded that the combination of PEG and PEG-HSA demonstrates particularly good properties as an efficient transmucosal absorption enhancer.

EXAMPLE 9

Investigation of Mechanism of Action of Solutol® HS15 as a Transmucosal Absorption Enhancer a) Cell Cultures Calu-3 cells were grown to confluence in 75 cm$^3$ flasks at 5% $CO_2$, 37° C. Once confluent, the cells were seeded onto Transwells° with plasma oxygen-treated polystyrene membranes (12 mm diameter, 0.4 µm pore size) at a seeding density of 100,000 cells per well. After seeding, the cells were maintained at 5% $CO_2$, 37° C. in EMEM supplemented with FBS (10%), antibiotic/antimycotic (final medium concentration 100 U/ml penicillin, 0.1 mg/ml streptomycin and 0.25 µg/ml amphotericin B) and L-Glutamine (final medium concentration 2 mM). During the culturing period, cell medium was changed every other day. Cell growth and tight junction formation was assessed by measurements of transepithelial electrical resistance (TEER—an indication of tight junction opening), which were performed every other day starting from day 7 post-seeding (daily TEER measurements were avoided due to the possibility of cell monolayer damage, both from the measurement process, and leakage of ions from electrodes). The background resistance was taken into account by measuring the resistance across 'blank' membranes (without cells) and subtracting this from the monolayer TEER.

Caco-2 cells were grown to confluence in 75 cm$^3$ flasks at 5% $CO_2$, 37° C. Once confluent, the cells were seeded onto Transwells° at a seeding density of 200,000 cells per well. After seeding, the cells were maintained at 5% $CO_2$, 37° C. in Dulbeco's Modified Eagles Medium (DMEM) supplemented with antibiotics/antimycotic, FBS and L-glutamine (as described for Calu-3 cells), which was changed every other day. A time period of 21 days was allowed in order for Caco-2 cells to fully differentiate. Cell growth and tight junction formation was assessed by TEER measurements, which was performed on day 21 post-seeding.

b) Measurement of TEER

TEER was measured using an EVOM Voltohmmeter (World Precision Instruments, UK), equipped with a pair of chopstick electrodes. Cell monolayers incubated with HBSS (pH 6.0 and 7.4 apical and basolateral, respectively) for the initial 2 hours and with EMEM (overnight) were used as the reference and the changes in TEER are reported as percentage relative to this reference. Background TEER due to the filter was deducted from the measurements. All experiments were performed in triplicates.

d) Effect of Solutol® HS15 on TEER

Solutol®HS15 was dissolved in HBSS/HEPES buffer pH 7.4 at the following concentrations: 0.10, 0.02, 0.005, 0.0001%, and applied to Calu-3 cells (human bronchial epithelial cell line). TEER was measured before the addition of Solutol® HS15 to provide baselines values and at a number of intervals following the addition of the Solutol® HS15 solutions. The cells were incubated with enhancer solutions for 2 hours after which the cells were washed and incubated with normal medium in order to assess TEER reversibility (a measure of toxicity).

Figure 6:
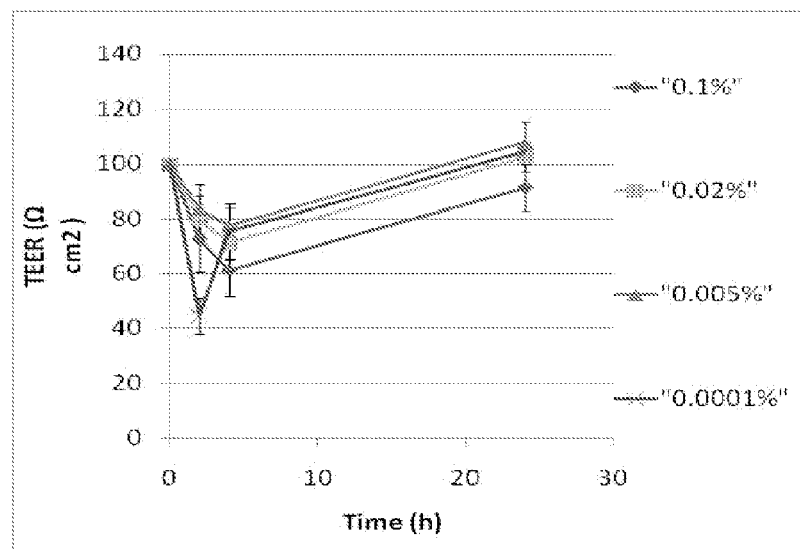
FIG. 6 shows the effect of Solutol® HS15 on transepithelial electrical resistance (TEER) when applied at different concentrations to a monolayer of Calu-3 cells.

The decrease in TEER after addition of the Solutol® HS15 solutions (see FIG. 6) to about 50% of the baseline value indicates that the Solutol® HS15 has a minor effect on tight junction opening. As a comparison, chitosan (a well known tight junction opener) decreased the TEER, under the same conditions, to about 5% of the baseline value.

e) Effect of Solutol® HS15 when Applied at Different Concentrations on FD4 Permeability Across Calu-3 and Caco-2 Cells Solutol® HS15 solutions were prepared at concentrations of 0.005, 0.02, 0.1% w/v in HBSS/HEPES buffer, pH 7.4 with FITC-dextran Mw 4400 (FD4). The solutions were applied to cell monolayers and two cell lines were used, Calu-3 cells (bronchial carcinoma) and Caco-2 cells (intestinal carcinoma). Apical to basolateral permeability of the FD4 was measured by regular basolateral sampling and the FD4 was quantified by fluorescence measurement.

Figure 7:
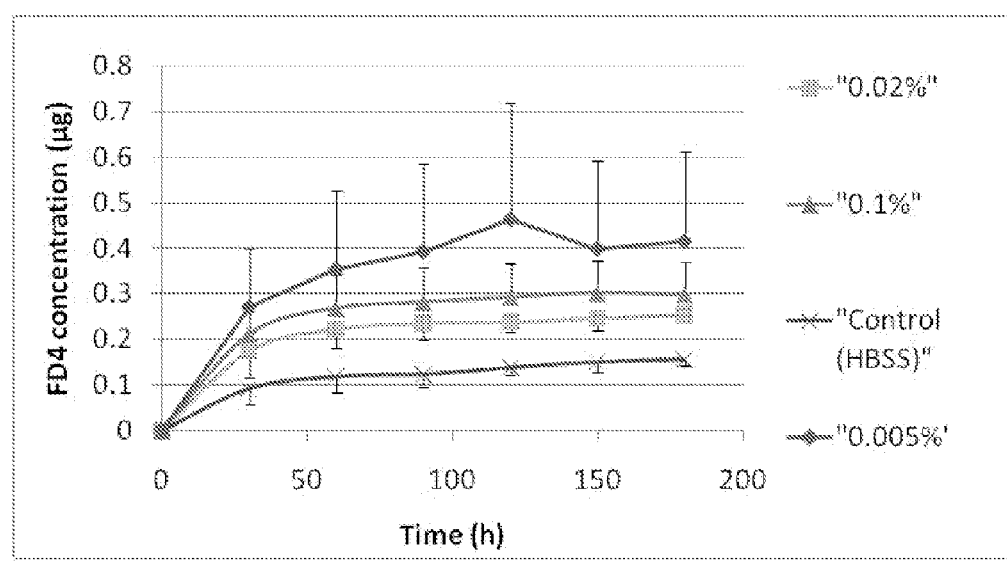
FIG. 7 shows the effect of Solutol® HS15 applied at different concentrations on FD4 permeability across Calu-3 cells.
Figure 8:
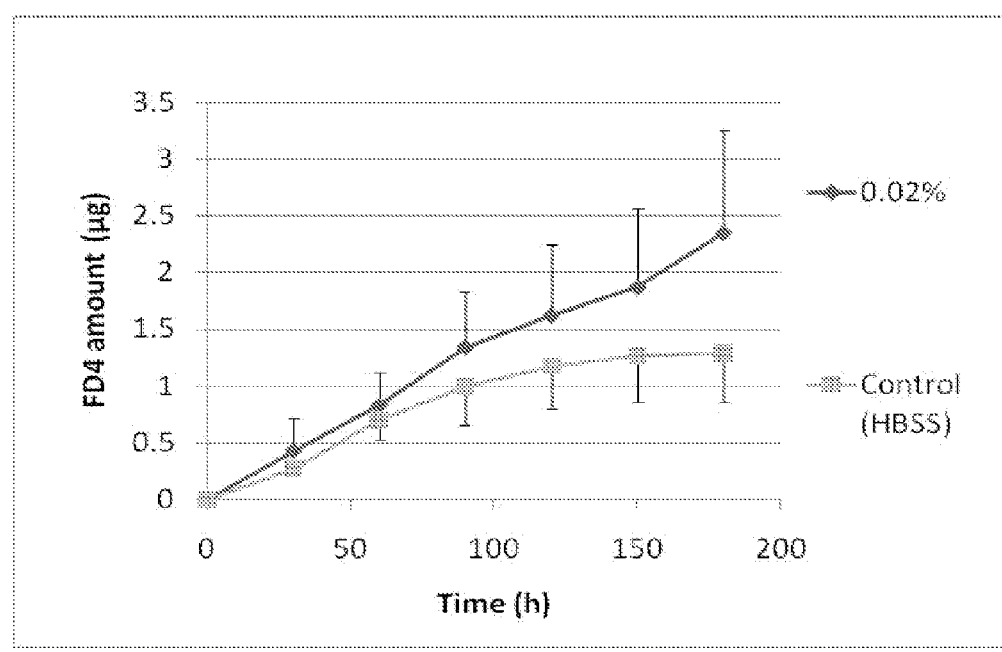
FIG. 8 shows the effect of Solutol® HS15 applied at different concentrations on FD4 permeability across Caco-2 cells.

FIG. 7 indicates that the basolateral FD4 concentration is higher when applied with the Solutol® HS15 solutions for the Calu-3 cell lines compared to the control solutions. However, statistical analysis of the data shows that there is no significant difference between the concentrations of Solutol® HS15 tested and the controls (p=0.093). As a comparison, under the same conditions chitosan showed a significant increase in permeability, 8 fold higher than for the control. As shown in FIG. 8, the increase in FD4 concentration for the Solutol® HS15 solution compared to the control is also not statistically significant (P=0.1473). It can therefore be concluded from the cell culture experiments that Solutol® HS15 has only a minor effect on tight junction opening. Hence, a transcellular pathway is likely to be the predominant mechanism of action.

The invention claimed is:

1. A pharmaceutical composition comprising:
   a therapeutic agent selected from the group consisting of growth hormone and parathyroid hormone; and
   an absorption enhancer comprising polyethylene glycol 660 hydroxy fatty acid ester;
   wherein the composition is in a form suitable for administration to the mucosal membranes of the nasal cavity, buccal cavity and/or respiratory tract, and the composition may not comprise liposomes, vesicles, micelles, or microemulsions.

2. A pharmaceutical composition comprising:
   a therapeutic agent selected from the group consisting of growth hormone and parathyroid hormone; and
   an absorption enhancer comprising polyethylene glycol 660 hydroxy fatty acid ester;
   wherein the composition is in the form of an aqueous solution or a dry powder that is suitable for administration to the mucosal membranes of the nasal cavity, buccal cavity and/or respiratory tract.

3. The composition according to claim 1, wherein the absorption enhancer further comprises free polyethylene glycol.

4. The composition according to claim 3, wherein the absorption enhancer comprises from about 30% to about 90% by weight of polyethylene glycol 660 hydroxy fatty acid ester, and from about 10% to about 50% by weight of free polyethylene glycol.

5. The composition according to claim 1, wherein the amount of absorption enhancer is at least 0.001% by weight of the total composition.

6. The composition according to claim 1, further comprising a bioadhesive agent, gelling agent and/or thickening agent.

7. The composition according to claim 1, wherein the pharmaceutical composition comprises one or more additional absorption enhancers.

8. The composition according to claim 7, wherein the additional absorption enhancer is selected from the group consisting of cyclodextrin, bile salts, poly-L-arginine, chitosan, phospholipids, lysophospholipids, polyacrylic acid, hyaluronic acids, sodium caprate and aminated gelatin.

9. The composition according to claim 2, wherein the composition is in the form of spray-dried or freeze-dried particles, microspheres or nanoparticles.

10. The composition according to claim 1, wherein the therapeutic agent is human growth hormone.

11. The pharmaceutical composition according to claim 2, wherein the therapeutic agent is human growth hormone.

12. The composition according to claim 1, wherein the amount of absorption enhancer present in the composition is at least 0.1% by weight of the total composition.

13. The composition according to claim 12, wherein the amount of absorption enhancer present in the composition is at most 40% by weight of the total composition.

14. The composition according to claim 13, wherein the amount of absorption enhancer present in the composition is 1 to 20% by weight of the total composition.

15. The composition according to claim 13, wherein the amount of absorption enhancer present in the composition is 2 to 15% by weight of the total composition.

16. The composition according to claim 13, wherein the amount of absorption enhancer present in the composition is 5 to 10% by weight of the total composition.

17. The composition according to claim 1, wherein the composition is in a form suitable for administration to the mucosal membranes of the nasal cavity and/or respiratory tract.

18. The composition according to claim 1, wherein the composition is in the form of a solution, gel, powder or nasal insert.

19. The composition according to claim 1, wherein the composition is in the form of a solution or dispersion in an aqueous medium, or a dry powder.

20. The composition according to claim 2, wherein the absorption enhancer further comprises free polyethylene glycol.

21. The composition according to claim 2, wherein the absorption enhancer comprises from about 30% to about 90% by weight of polyethylene glycol 660 hydroxy fatty acid ester, and from about 10% to about 50% by weight of free polyethylene glycol.

22. The composition according to claim 2, wherein the amount of absorption enhancer is at least 0.001% by weight of the total composition.

23. The composition according to claim 2, wherein the amount of absorption enhancer present in the composition is at least 0.1% by weight of the total composition.

24. The composition according to claim 23, wherein the amount of absorption enhancer present in the composition is at most 40% by weight of the total composition.

25. The composition according to claim 2, further comprising a bioadhesive agent, gelling agent and/or thickening agent.

26. The composition according to claim 2, wherein the pharmaceutical composition comprises one or more additional absorption enhancers.

27. The composition according to claim 26, wherein the additional absorption enhancer is selected from the group consisting of cyclodextrin, bile salts, poly-L-arginine, chitosan, phospholipids, lysophospholipids, polyacrylic acid, hyaluronic acids, sodium caprate and aminated gelatin.

* * * * *